(12) United States Patent
Wada et al.

(10) Patent No.: US 9,574,165 B2
(45) Date of Patent: Feb. 21, 2017

(54) CELL CULTURE APPARATUS AND CELL CULTURE METHOD USING THE SAME

(71) Applicants: ABLE CORPORATION, Tokyo (JP); TOKYO WOMEN'S MEDICAL UNIVERSITY, Tokyo (JP)

(72) Inventors: Masanori Wada, Tokyo (JP); Katsuhisa Matsuura, Tokyo (JP); Tatsuya Shimizu, Tokyo (JP); Teruo Okano, Tokyo (JP); Hiroyuki Tsurii, Tokyo (JP)

(73) Assignees: ABLE CORPORATION, Tokyo (JP); TOKYO WOMEN'S MEDICAL UNIVERSITY, Tokyo (JP)

( * ) Notice: Subject to any disclaimer, the term of this patent is extended or adjusted under 35 U.S.C. 154(b) by 0 days.

(21) Appl. No.: 14/407,413

(22) PCT Filed: Jun. 10, 2013

(86) PCT No.: PCT/JP2013/065946
§ 371 (c)(1),
(2) Date: Dec. 11, 2014

(87) PCT Pub. No.: WO2013/187359
PCT Pub. Date: Dec. 19, 2013

(65) Prior Publication Data
US 2015/0252315 A1    Sep. 10, 2015

(30) Foreign Application Priority Data

Jun. 11, 2012  (JP) ................................ 2012-131597

(51) Int. Cl.
*C12M 1/06*    (2006.01)
*C12M 1/24*    (2006.01)
(Continued)

(52) U.S. Cl.
CPC .......... *C12M 27/02* (2013.01); *B01F 13/0872* (2013.01); *B01F 15/00175* (2013.01);
(Continued)

(58) Field of Classification Search
CPC ...... C12M 27/02; C12M 41/12; C12N 23/006; C12N 23/08; B01F 3/0872; B01F 15/00175
(Continued)

(56) References Cited

U.S. PATENT DOCUMENTS 2,572,375 A    10/1951  Oertli ............................ 259/108
4,173,310 A *  11/1979  Schaeffer ............ A47J 43/0722
                                                          241/282.1
(Continued)

FOREIGN PATENT DOCUMENTS

CN    201762330    3/2011  .............. C12M 3/00
JP    2002-331234  11/2002  .............. B01F 15/00
(Continued)

OTHER PUBLICATIONS

European Search Report dated Jan. 4, 2016 in EP Application No. 13804267.6 in PCT/JP2013/065946 with English translation.
(Continued)

*Primary Examiner* — Michael Hobbs
(74) *Attorney, Agent, or Firm* — Harness, Dickey & Pierce, P.L.C.

(57) ABSTRACT

Disclosed herein is a cell culture apparatus that can achieve appropriate culture conditions. The cell culture apparatus (1) includes: a cylindrical culture vessel (10) that holds a culture liquid containing cells; a supporting column (20) that stands upright in a center of an inner surface of a bottom (12) in the culture vessel; and a stirring device (30) that includes an attaching portion (32) that is attached to an upper portion of the supporting column so as to be rotatable relative to the
(Continued)

supporting column and a stirring blade (34) whose upper portion is fixed to the attaching portion so as to rotate around the supporting column.

12 Claims, 10 Drawing Sheets

(51) Int. Cl.
C12M 1/12 (2006.01)
C12M 1/34 (2006.01)
B01F 13/08 (2006.01)
B01F 15/00 (2006.01)

(52) U.S. Cl.
CPC ............ *C12M 23/06* (2013.01); *C12M 23/08* (2013.01); *C12M 41/12* (2013.01)

(58) Field of Classification Search
USPC ...................................................... 435/289.1
See application file for complete search history.

(56) References Cited

U.S. PATENT DOCUMENTS

| | | | | |
|---|---|---|---|---|
| 4,194,697 A * | 3/1980 | Lembeck | ................ | A47J 43/06 222/352 |
| 6,109,780 A | 8/2000 | Lesniak | ......................... | 366/253 |
| 6,428,199 B1 | 8/2002 | Rupaner et al. | ........... | 366/172.1 |
| 8,057,092 B2 | 11/2011 | Ryan et al. | .................... | 366/274 |
| 2005/0087002 A1 | 4/2005 | Kanzaki et al. | ............. | 73/54.28 |
| 2008/0131957 A1 | 6/2008 | Ryan et al. | ................ | 435/289.1 |

FOREIGN PATENT DOCUMENTS

| | | | | |
|---|---|---|---|---|
| JP | 2004-534544 | 11/2004 | ............ | C12M 1/00 |
| JP | 2007-021497 | 2/2007 | ............ | B01F 13/08 |
| KR | 2012-0098123 | 9/2012 | ............. | C12M 1/02 |
| WO | WO 03/006633 | 1/2003 | ............... | C12N 5/02 |
| WO | WO 2005/068059 | 7/2005 | ................ | B01F 3/04 |

OTHER PUBLICATIONS

International Preliminary Report on Patentability for PCT/JP2013/065946, dated Dec. 18, 2014 with English Translation.
Haraguchi, et al. (2011) "Examination of the large-scale suspension culture method of human iPS cells." *Regenerative Medicine*, vol. 10(Suppl.):198 (1P-027) with English translation.
Haraguchi et al. (2012), "Examination of the suspension culture and cardiac differentiation methods of human iPS cells." *Regenerative Medicine*, vol. 11(Suppl.):211 (O-33-6) with English translation.
Olmer, et al. (2012) "Suspension culture of human pluripotent Stem cells in controlled, stirred bioreactors." [online] *Tissue Engineering Part C Methods*, Apr. 20, 2012 [Epub ahead of print] [searched on May 10, 2012], Internet <URL: http://www.ncbi.nlm.nih.gov/pubmed>.
Olmer, et al. (2012) "Suspension culture of human pluripotent Stem cells in controlled, stirrer bioreactors." *Tissue Engineering: Part C*, vol. 18(10):772-784.
Rungarunlert et al. (2009) "Embryoid body formation from embryonic and induced pluripotent stem cells: Benefits of bioreactors." *World J Stem Cells* vol. 1(1):11-21.
Valamehr, et al. (2008) "Hydrophobic surfaces for enhanced differentiation of embryonic stem cell-derived embryoid bodies." *PNAS*, vol. 105(38):14459-14464.
Willems, et al. (2011) "Small-molecule inhibitors of the Wnt pathway potently promote cardiomyocytes from human embryonic stem cell-derived mesoderm." *Circ Res.*, vol. 109(4):360-364.
International Search Report (ISR) dated Sep. 10, 2013 in PCT/JP2013/065946 with English translation.

* cited by examiner

CELL CULTURE APPARATUS AND CELL CULTURE METHOD USING THE SAME

CROSS-REFERENCE TO RELATED APPLICATIONS

This application is a national phase application of PCT Application No. PCT/JP2013/065946 filed on Jun. 10, 2013, which claims the benefit and priority to Japanese Patent Application No. 2012-131597 filed Jun. 11, 2012. The entire disclosures of the applications identified in this paragraph are incorporated herein by references.

FIELD

The present invention relates to a cell culture apparatus useful in the fields of drug discovery, pharmacy, medicine, organism and the like, and a cell culture method using the same.

BACKGROUND

Pluripotent stem cells, such as embryonic stem cells (ES cells) and induced pluripotent stem cells (iPS cells), can differentiate into cells of all tissues and organs of living body, and therefore have been actively researched and developed in recent years. These pluripotent stem cells have potential as a new supply source of cells for cell therapy, and therefore expectations for their clinical applications are increasing. However, since pluripotent stem cells have the ability to differentiate into various tissue cells, it is difficult to culture and amplify a large amount of pluripotent stem cells while maintaining their undifferentiated state. Therefore, pluripotent stem cells need to be cultured by a method different from a conventional culture method.

As a method for culturing and amplifying pluripotent stem cells while maintaining their undifferentiated state, a method is known in which cell aggregates called embryoid bodies (EBs) are formed and cultured. This is a culture method in which cellular aggregates are formed in imitation of the embryo of a vertebrate formed by repeated cleavage after fertilization. Embryo development is imitated by forming embryoid bodies, and differentiation of the embryoid bodies into any cells can be induced by adding various growth factors etc.

In order to induce differentiation of ES cells or iPS cells, embryoid bodies from these cells need to be formed. Various methods are known for forming embryoid bodies (see Non Patent Literature 1). Examples of a method for forming embryoid bodies include: a method using a culture dish having low cell-adhesive properties, a method called "hanging-drop method" in which a culture liquid containing cells is applied to the cover of a culture dish, and a stirred-suspension culture method. Three-dimensional-stirred suspension culture allows process control and is suitable for scale-up. On the other hand, particularly human-derived ES/iPS cells are very sensitive to shear stress, and therefore stirred-suspension culture requires a stirring device that can achieve a low shear stress. For this reason, a measure such as reducing the blade area of a stirring impeller or reducing the tip speed of a blade during stirring is taken. During embryoid body formation, ES cells or iPS cells grow within embryoid bodies while maintaining their undifferentiated state so that the specific gravity of the embryoid bodies increases. Therefore, when such a measure is uniformly taken, desired cells cannot be obtained in good yield due to non-uniform culture. Its major cause is that the embryoid bodies aggregate in an area in a culture vessel where a liquid flow is not uniform, and therefore the specific gravity of the embryoid bodies further increases so that stirred-suspension itself cannot be performed.

Embryoid bodies having too large a particle size bring cells within the embryoid bodies into a state of ischemia (low nutrition, low oxygen), which promotes cell death and interferes with uniform penetration (diffusion) of a differentiation-inducing factor added to a culture medium into the embryoid bodies. It is said that cell aggregates such as embryoid bodies preferably have a diameter of about 200 μm to successfully supply oxygen and nutrients to their central part and to differentiate into any cells. Therefore, it is important for induction of differentiation of cell aggregates such as embryoid bodies into any cells to obtain and culture a population of cell aggregates (e.g., embryoid bodies) having a uniform particle size of 100 to 300 μm in the process of embryoid body formation (see Non Patent Literature 2). When cell aggregates non-uniform in particle size are formed, nutrients, oxygen, differentiation-inducing factors, etc. added to induce differentiation into any cells cannot penetrate into the cell aggregates, which inhibits cell growth and differentiation induction.

From the viewpoint of liquid flow, the following conventional culture methods are generally used: a method (axial-flow culture) in which a vertical flow along a stirring shaft is created using a stirring impeller having two or more blades attached at a given inclination angle with respect to the stirring shaft (see Non Patent Literature 3); and a method (laminar-flow culture) in which a horizontal flow (with a doughnut shape as seen from above) is created by rotating several large paddles that stand perpendicular to the inner surface of bottom of a culture vessel or by rotating a stirring shaft having a thick bulb-shaped tip. FIG. 4 is a schematic sectional view of a cell culture apparatus equipped with a paddle-type stirring impeller as one example of a cell culture apparatus equipped with a stirring impeller having two or more blades attached at a given inclination angle with respect to a stirring shaft. FIG. 3 is a schematic sectional view of a cell culture apparatus manufactured by INTEGRA as one example of a cell culture apparatus in which a horizontal flow is created by rotating a stirring shaft having a thick bulb-shaped tip. Both the cell culture apparatuses will be described later.

Axial-flow culture requires a stirring impeller having many blades to uniformly stir the entire culture liquid in a culture vessel at a low speed, and therefore there is a fear that shear stress caused by rotation increases. Further, stagnation is likely to occur directly below a shaft because of the structure of the stirring impeller, and therefore there is also a problem that cell aggregates (e.g., embryoid bodies) having an increased specific gravity due to cell growth precipitate and therefore cell aggregates uniform in particle size are difficult to obtain. Laminar-flow culture can easily achieve stirring at a very low shear stress by setting a rotation speed to a level such that a turbulent flow does not occur, but has a problem that stagnation is easily to occur in the center of a doughnut-shaped liquid flow.

Various sensors that measure pH, dissolved oxygen (DO), temperature, etc. are inserted into a culture vessel during culture. However, when pluripotent stem cells are cultured in a small volume of culture liquid of about several tens of milliliters to 100 mL, there is a fear that conventional sensors interfere with uniform stirring because their excluded volumes are too large with respect to the volume of the culture liquid. Therefore, in order to achieve appropriate culture conditions, the shape, structure, or arrangement of various sensors as well as the shape of a culture vessel or stirring blade needs to be devised so that the sensors do not interfere with uniform stirring. The temperature sensor is conventionally inserted into a sheath tube inserted into a culture vessel through the top plate of the culture vessel so that its tip is located several tens of millimeters below the liquid level of the culture vessel to indirectly measure a liquid temperature. The temperature sensor includes a stainless-steel sheath tube having a closed tip, and there is, generally, a temperature-sensitive part for measuring temperature in a position several millimeters away from the tip, in which a resistance temperature detector or the like is embedded. When the temperature sensor has a diameter of 3 mm, the tip of the sensor is usually located 15 mm (five times the diameter of the temperature sensor) below the liquid level. If the depth of the tip of the sensor is less than 15 mm, the liquid temperature cannot be accurately measured, and if the depth of the tip of the sensor exceeds 15 mm, the sensor interferes with uniform stirring. Further, there is trouble that an operator makes the mistake of not inserting the temperature sensor into the sheath tube, which causes overheating of a culture liquid and results in the failure of culture. Even if an operator forgets to connect the pH or DO sensor to a sensor connector, since the value of pH or DO slowly changes, there is a low possibility that culture ends in failure when the operator quickly discovers and addresses the mistake. However, when an operator forgets to insert the temperature sensor, since the cell culture apparatus cannot determine whether a temperature reading is the temperature of the culture liquid or a room temperature, there is a case where the temperature of the culture liquid exceeds 50° C. before the operator discovers the mistake. Culture of pluripotent stem cells uses an expensive culture medium and needs a long period of time, and therefore there has been a strong user demand for measures directed toward elimination of mistakes in the operation of setting a temperature sensor in a culture vessel.

CITATION LIST

Non Patent Literatures

Non Patent Literature 1: Sasitorn Rungarunlert et al., World J Stem Cells 1(1): 11-21 (2009)

Non Patent Literature 2: Bahram Valamehr et al., PNAS 105, 38 (2008)

Non Patent Literature 3: Olmer R et al., Suspension culture of human pluripotent Stem cells in controlled, stirrer bioreactors, [online], Tissue Engineering Part C Methods. 2012 Apr. 20. [Epub ahead of print] [searched on May 10, 2012], Internet <URL: http://www.ncbi.nlm.nih.gov/pubmed>

Non Patent Literature 4: Willems et al., Circulation Research, USA, American Heart Association, Jul. 7, 2011, 109(4), p. 360-364

SUMMARY OF INVENTION

Technical Problem

The present invention is made to solve the above problems, and it is an object of the present invention to provide a cell culture apparatus that can achieve appropriate culture conditions. Specifically, it is an object of the present invention to provide a cell culture apparatus that can culture cells at a low shear stress in a laminar flow without the stagnation of liquid flow in a culture vessel, especially near the center of bottom of the culture vessel, and therefore can easily and reproducibly provide a population of cell aggregates (e.g., embryoid bodies) uniform in particle size. Further, it is also an object of the present invention to provide a cell culture apparatus that can provide a population of cell aggregates (e.g., embryoid bodies) whose differentiation into any cells is efficiently induced. Further, it is also an object of the present invention to provide a cell culture apparatus equipped with a temperature sensor that can measure the temperature of a culture liquid without interfering with uniform stirring.

Further, it is also an object of the present invention to provide a cell culture method that easily and reproducibly provides a population of cell aggregates uniform in particle size with the use of the cell culture apparatus according to the present invention. Further, it is also an object of the present invention to provide a cell culture method that efficiently induces differentiation of pluripotent stem cells into somatic cells.

Technical Solution

Hereinbelow, means for achieving the above objects of the present invention will be described. It is to be noted that reference signs shown in the accompanying drawings are provided in parentheses to aid understanding of the present invention, which is not intended to limit the present invention to embodiments shown in the drawings.

To achieve the above objects, a cell culture apparatus (1, 101, 201, 301) according to the present invention includes: a cylindrical culture vessel (10, 110, 210) that holds a culture liquid containing cells; a supporting column (20, 120, 220, 320) that stands upright in a center of an inner surface of a bottom (12, 112, 212) of the culture vessel; and a stirring device (30, 130, 230) including an attaching portion (32, 132) that is attached to an upper portion (24, 124, 324) of the supporting column so as to be rotatable relative to the supporting column and a stirring blade (34, 134) whose upper portion is fixed to the attaching portion so as to rotate around the supporting column as a center of rotation.

The present invention is characterized in that the supporting column may have a conical portion (22, 122), the conical portion having a portion conically formed to rise up from the inner surface of the bottom and the conical portion having a diameter increasing toward the inner surface of the bottom, and the upper portion of the supporting column may be located above a liquid level of the culture liquid. In this case, since an area near the center of the bottom due to the rotation of the culture liquid is occupied by the conical portion (this conical portion functions as a spacer), there is no possibility that the stagnation of liquid flow occurs near the center of the bottom, which makes it possible to prevent cell aggregates (e.g., embryoid bodies) from precipitating near the center of the bottom due to their increase in volume. Further, there is virtually no possibility that cell aggregates enter into a sliding portion between the upper portion of the supporting column and the attaching portion (32, 132) rotatably attached to the upper portion of the supporting column, which makes it possible to prevent physical disruption of cell aggregates or cell death due to a strong shear force.

Further, the present invention is characterized in that the stirring blade of the stirring device may be formed so that its lower portion has a shape that conforms an outer surface of the conical portion of the supporting column when the stirring device rotates. This makes it possible to more reliably prevent precipitating of cell aggregates on the conical portion.

Further, the present invention is characterized in that the stirring blade of the stirring device may be formed to have a shape that conforms to the inner surface of the bottom in the culture vessel when the stirring device rotates. This makes it possible to prevent precipitating of cell aggregates on the inner surface of the bottom.

Further, the present invention is characterized in that the stirring blade of the stirring device may be formed to have a shape that conforms to an inner side surface (14, 114) of the culture vessel when the stirring device rotates. This makes it possible to create a uniform laminar flow and therefore to prevent settling of cell aggregates that easily settle.

That is, an ideal laminar flow has the same flow rate at every position in the longitudinal section of a liquid layer. For this reason, the stirring blade preferably has a shape that conforms to the inner side surface of the culture vessel.

Further, the cell culture apparatus may further include a drive device (50; 52, 150; 154, 250; 252) that rotates the stirring blade of the stirring device without direct contact with the culture liquid. This makes it possible to stir the culture liquid without fear of contamination.

Further, the stirring blade of the stirring device may have a magnetic body (36) fixed to its lower end, and the drive device (50) provided below the culture vessel may include a drive device (52) that is another magnetic body that is horizontally rotated in a position opposed to the magnetic body with the bottom of the culture vessel interposed therebetween so that the stirring blade is horizontally rotated by rotating the another magnetic body. In this case, when the another magnetic body is horizontally rotated, the stirring blade in the culture vessel can be horizontally rotated from the outside of the culture vessel due to the magnetic attractive action of the upper and lower two magnetic bodies between which the bottom of the culture vessel is interposed.

It is to be noted that when both the upper and lower magnetic bodies are permanent magnets, they are arranged so that different magnetic poles are opposed to each other.

Further, the drive device may be provided below the culture vessel, and a drive shaft (154) of the drive device may pass through an inside of the supporting column, extend to the upper portion of the supporting column, and be attached to the stirring blade of the stirring device at the upper portion. This makes it possible to directly transmit the torque of the drive device to the stirring blade.

Further, the supporting column may have, in its inside, a hole (220*a*) into which a temperature-sensitive part (240) of a temperature sensor (280) that measures a temperature of the culture liquid is inserted from an outer surface side of the bottom of the culture vessel. In this case, the temperature-sensitive part of the temperature sensor that measures the temperature of the culture liquid without interfering with uniform stirring can be placed in the hole, that is, in an appropriate position where the temperature of the culture liquid in the culture vessel can be measured.

Further, the cell culture apparatus may further include the temperature-sensitive part of the temperature sensor. In this case, the temperature of the culture liquid can be measured by the temperature-sensitive part of the temperature sensor that is previously inserted into the hole of the supporting column.

Further, the temperature-sensitive part of the temperature sensor may be placed 20 to 30 mm away from an outer surface (212) of the bottom of the culture vessel (210). In this case, the temperature of the culture liquid can be measured without external influence.

The present invention is directed also to a cell culture method using the cell culture apparatus according to the present invention, the method including a first process in which cells that form cell aggregates are inoculated into the culture vessel together with a culture medium; and a second process in which the cells are cultured by rotating the stirring device at a speed such that cell aggregates do not precipitate on the inner surface of the bottom of the culture vessel and that the cell aggregates are not broken up, wherein the cells are cultured while the cell aggregates maintain their uniform particle size. According to this cell culture method, it is possible to easily and reproducibly obtain a population of cell aggregates uniform in particle size.

The cell culture method may further include, when the cells that form cell aggregates are pluripotent stem cells, a third process in which the cells are cultured by adding, to the culture medium, a factor that induces differentiation into somatic cells, wherein differentiation of the pluripotent stem cells into somatic cells is induced. According to this cell culture method, it is possible to easily and reproducibly obtain a population of cell aggregates uniform in particle size, and further it is possible to improve the efficiency of induction of differentiation of pluripotent stem cells into somatic cells.

Advantageous Effects

According to the present invention having the above-described features, it is possible to provide a cell culture apparatus that can achieve appropriate culture conditions. Specifically, it is possible to provide a cell culture apparatus that can culture cells at a low shear stress in a laminar flow without the stagnation of liquid flow in a culture vessel, especially near the center of bottom of the culture vessel, and therefore can easily and reproducibly provide a population of cell aggregates (e.g., embryoid bodies) uniform in particle size. Further, it is also possible to provide a cell culture apparatus that can provide a population of cell aggregates (e.g., embryoid bodies) whose differentiation into any cells is efficiently induced. Further, it is also possible to provide a cell culture apparatus equipped with a temperature sensor that can measure the temperature of a culture liquid without interfering with uniform stirring.

Further, it is also possible to provide a cell culture method that easily and reproducibly provides a population of cell aggregates uniform in particle size with the use of the cell culture apparatus according to the present invention. Further, it is also possible to provide a cell culture method that efficiently induces differentiation of pluripotent stem cells into somatic cells.

DESCRIPTION OF EMBODIMENTS (First Embodiment)

Figure 1:
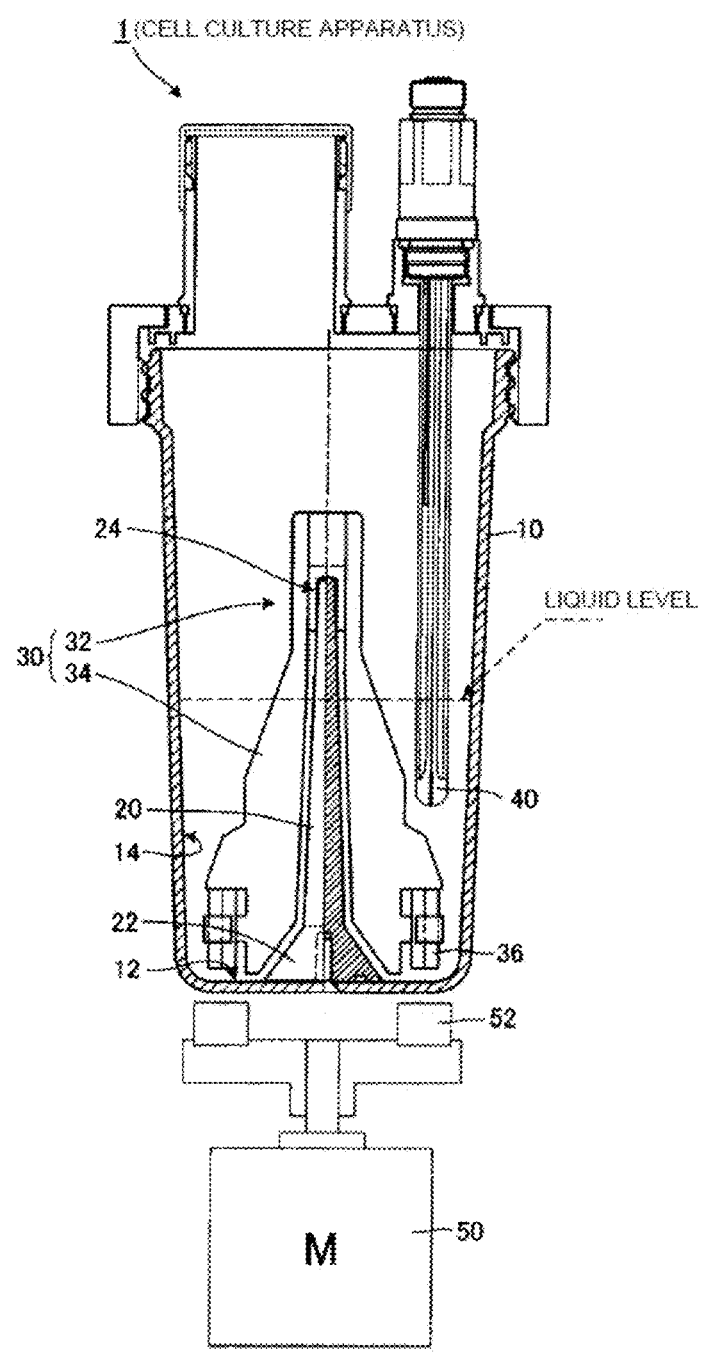
FIG. 1 is a sectional view that illustrates the entire structure of a cell culture apparatus according to a first embodiment of the present invention.

Hereinbelow, embodiments for implementing the present invention will be described with reference to the accompanying drawings. FIG. 1 is a sectional view illustrating the entire structure of a cell culture apparatus 1 according to a first embodiment. The cell culture apparatus 1 includes a cylindrical culture vessel 10, a supporting column 20 fixed to stand upright in the culture vessel 10, and a stirring device 30 rotatably attached to the supporting column 20. The culture vessel 10 is equipped with a pH sensor 40 as one example of a measuring device that is submerged in a culture liquid to measure the condition of the culture liquid. The cell culture apparatus 1 further includes a drive motor 50 as one example of a drive device that rotates a stirring blade 34 (which has a magnetic body (e.g., a permanent magnet) 36 fixed to the lower end thereof (described later)) of the stirring device 30 and a drive device 52 that is another magnetic body (e.g., a permanent magnet). The drive motor 50 and the another magnetic body 52 are provided under the culture vessel 10.

It is to be noted that, as described above, when both the upper and lower magnetic bodies are permanent magnets, they are arranged so that different magnetic poles are opposed to each other.

The culture vessel 10 holds a culture liquid containing cells. The culture vessel 10 is preferably made of a material that is inactive against the components of the culture liquid, has no cytotoxity, and has resistance to sterilization (also referred to as decontamination, disinfection, or aseptic) treatment. Examples of such a material include glass, synthetic resins, and stainless steel. Here, the internal capacity, shape, etc. of the culture vessel 10 are appropriately determined according to the amount of the culture liquid. The internal capacity (full capacity) of the culture vessel 10 is not particularly limited, but may be, for example, 20 ml to 1000 ml. From the viewpoint of the efficiency of stirring and aeration, the culture vessel 10 is preferably designed to have a shape such that when a desired amount of the culture liquid is fed into the culture vessel, the ratio between the inner diameter of the culture vessel and the depth of the culture liquid in the culture vessel is 1:1 and the predetermined amount of the culture liquid is about half the internal capacity.

The supporting column 20 is fixed to stand upright in the center of inner surface of a bottom 12 in the culture vessel 10. The supporting column 20 is preferably made of a material that is inactive against the culture liquid and has resistance. Examples of such a material include synthetic resins and stainless steel. The supporting column 20 has a conical portion 22 that is conically formed as a portion fixed to the inner surface of the bottom 12 in the culture vessel 10 so as to have a diameter increasing downward. Therefore, there is no possibility that the stagnation of liquid flow occurs in an area near the center of the bottom due to the rotation of the culture liquid, because the area is occupied by the conical portion 22. Therefore, precipitating of cell aggregates having an increased specific gravity due to cell growth does not occur.

It is to be noted that a method for fixing the supporting column 20 so that the supporting column 20 stands upright in the center of the inner surface of the bottom 12 in the culture vessel 10 as shown in FIG. 1 is not particularly limited. However, when being provided as separate components as shown in FIG. 1, the culture vessel 10 and the supporting column 20 may be screwed and fixed by screws 22b with an O-ring 22a being interposed therebetween or may be adhered and fixed with a heat-resistant adhesive (e.g., silicone rubber-based adhesive) (not shown). Alternatively, the culture vessel 10 and the supporting column 20 may be integrally molded.

An upper portion 24 of the supporting column 20 is located above the liquid level of the culture liquid, and the stirring device 30 is rotatably attached to the upper portion 24.

It is to be noted that the thickness of a portion of the supporting column 20 extending from the top of the conical portion 22 to the upper portion 24 is not particularly limited. However, from the viewpoint of ensuring the strength of the supporting column 20, such a portion preferably is thickened at its lower part and has a diameter gradually decreasing from its bottom to top.

The stirring device 30 includes an attaching portion 32 and the stirring blade 34. The attaching portion 32 is attached to the upper portion 24 of the supporting column 20 so as to be rotatable relative to the supporting column 20, and the stirring blade 34 is fixed to the attaching portion 32 at its upper portion so as to rotate around the supporting column 20 as a center of rotation in the culture vessel 10. The attaching portion 32 is preferably made of a material that is inactive against the culture liquid and has resistance. Examples of such a material include synthetic resins and stainless steel. The stirring blade 34 is also preferably made of a plate material that is inactive against the culture liquid and has resistance. Examples of such a plate material include thin plates made of a synthetic resin or stainless steel (e.g., 1 mm-thick SUS316). The stirring blade 34 of the stirring device 30 has the magnetic body (e.g., permanent magnet) 36 at its lower end on the side closer to the inner wall of the culture vessel 10. The magnetic body 36 is coated with tetrafluoroethylene or the like, and is fixed and held by a bent lower end portion of the stirring blade 34.

Here, in FIG. 1, the two left and right stirring blades 34 are shown, but the present invention is not limited thereto. The number of the stirring blades 34 depends on the number of rotations of the stirring device, but the stirring blades 34 are preferably provided at regular intervals around the supporting column 20 from the viewpoint of the balance of the stirring blades 34 during stirring. For example, the number of the stirring blades 34 is preferably 2 to 4.

The stirring blade 34 of the stirring device 30 is formed so that the gap between the stirring blade 34 and the conical portion 22 of the supporting column 20 is small, and therefore when the stirring device 30 rotates, the stirring blade 34 conforms to the outer surface (surface) of the conical portion 22. This makes it possible to rotate the culture liquid near the conical portion 22 to suspend the cells in the culture liquid, thereby more reliably preventing cell aggregates from precipitating near the conical portion 22. Further, the stirring blade 34 is formed so that the gap between the stirring blade 34 and the inner surface of the bottom 12 in the culture vessel 10 is small, and therefore when the stirring device 30 rotates, the stirring blade 34 conforms to the inner surface of the bottom 12. This makes it possible to stir the culture liquid near the inner surface of the bottom 12 to continuously suspend the cells and cell aggregates in the culture liquid, thereby preventing the cell aggregates from settling on the inner surface of the bottom 12. Further, the stirring blade 34 is formed so that the gap between the stirring blade 34 and an inner side surface 14 of the culture vessel 10 is small, and therefore when the stirring shaft 30 rotates, the stirring blade 34 conforms to the inner side surface 14. This makes it possible to stir the culture liquid near the inner side surface 14 to create a uniform laminar flow, thereby preventing precipitating of cell aggregates having an increased specific gravity due to cell growth. It is to be noted that at this time, the stirring blade preferably has a shape that conforms to at least the lower portion of the inner side surface and its vicinity.

Further, the stirring blade 34 is preferably formed so that the gap between a portion of the stirring blade 34 facing the supporting column 20 and the supporting column 20 is small. In this case, when the stirring device 30 rotates, the stirring blade 34 conforms to the outer surface of the supporting column 20. This makes it possible to ensure a uniform liquid flow near the supporting column 20, thereby achieving a more uniform liquid flow in the entire culture liquid.

The drive motor (drive device) 50 and the another magnetic body (permanent magnet) (drive device) 52 are provided outside and under the culture vessel 10. The drive motor 50 is placed so that its rotary shaft is concentric with the supporting column 20. The another magnetic body 52 is attached so as to face the magnetic body 36 attached to the lower end of the stirring blade 34 with the bottom of the culture vessel 10 being interposed therebetween and so as to be horizontally rotated by the drive motor 50. When the another magnetic body 52 is horizontally rotated by the drive motor 50, the stirring blade 34 of the stirring device 30 is rotated around the supporting column 20 by the magnetic force of the another magnetic body 52 and the magnetic force of the magnetic body 36 attached to the lower end of the stirring blade 34. Here, the drive motor 50 is preferably, for example, a servomotor whose rotational speed can be controlled.

It is to be noted that when the magnetic body 36 and the another magnetic body 52 provided inside and outside the culture vessel 10 are permanent magnets, they are arranged so that different magnetic poles (N pole and S pole) that attract each other are opposed to each other.

Further, the number of rotations of the stirring device during cell culture is not particularly limited, and is appropriately selected and used so that a low shear stress, prevention of precipitating of cell aggregates and the like are ensured. For example, the number of rotations of the stirring device during cell culture is preferably 10 to 80 rpm.

The pH sensor 40 is positioned so that its tip is submerged in the culture liquid to measure the pH of the culture liquid. The stirring blade 34 is formed to have a shape such that when the stirring device 30 rotates, the stirring blade 34 does not contact with the pH sensor 40 and avoids the pH sensor 40. The stirring blade 34 having such a structure does not interfere with the rotation of the stirring device 30.

It is to be noted that if necessary, various tools, etc., may be inserted into the culture vessel through the top plate of the culture vessel, a sterilization filter may be provided at an opening, and/or various optical sensor chips (e.g., dissolved oxygen level measurement) whose submerged portions have an extremely small excluded volume may be provided in the culture vessel so as not to affect an ideal laminar flow.

(Second Embodiment)

Figure 2:
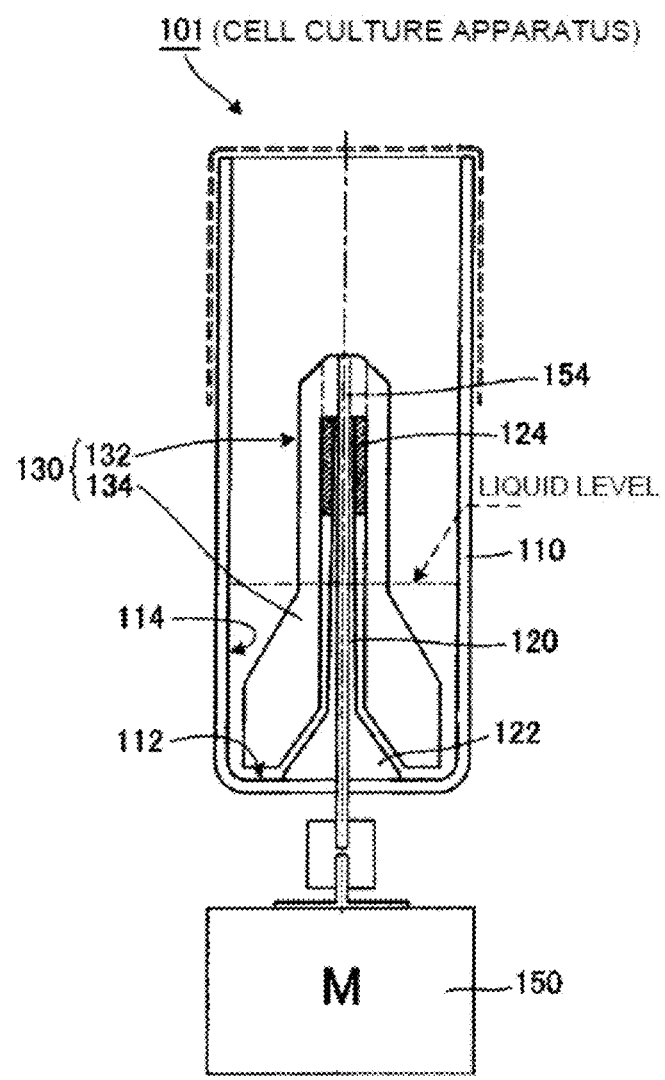
FIG. 2 is a sectional view that illustrates the entire structure of a cell culture apparatus according to a second embodiment of the present invention.

FIG. 2 is a sectional view illustrating the entire structure of a cell culture apparatus 101 according to a second embodiment. The description of components similar to those of the cell culture apparatus 1 according to the first embodiment shown in FIG. 1 will not be repeated by giving similar reference numerals. The cell culture apparatus 101 includes a culture vessel 110, a supporting column 120, and a stirring device 130. The cell culture apparatus 101 further includes a drive motor 150 and a drive shaft 154 as one example of a drive device. The cell culture apparatus 101 according to the second embodiment shown in FIG. 2 is different from the cell culture apparatus 1 shown in FIG. 1, in which torque is transmitted by magnetic force, in that the drive shaft 154 of the drive motor 150 provided under the culture vessel 110 passes through the inside of the supporting column 120, extends to an upper portion 124, and is directly attached to a stirring blade 134. Further, the cell culture apparatus 101 shown in FIG. 2 is different from the cell culture apparatus 1 shown in FIG. 1 also in that a pH sensor is not provided.

The supporting column 120 is fixed to stand upright in the center of the inner surface of a bottom 112 in the culture vessel 110. The supporting column 120 has a conical portion 122 in its lower portion. The stirring device 130 includes an attaching portion 132 rotatably attached to the upper portion 124 of the supporting column 120 and the stirring blade 134.

It is to be noted that the stirring blade 134 shown in FIG. 2 has a wide lower portion and a narrow upper portion. However, the shape of the stirring blade 134 in a direction toward the inner surface of the culture vessel is not particularly limited. For example, the upper and lower portions of the stirring blade 134 may have the same width as long as there is no tool, etc., inserted into the culture vessel through the top plate of the culture vessel.

Further, in the cell culture apparatus 101, the drive shaft 154 is directly attached to the stirring blade 134 in the upper portion 124 of the supporting column 120, and therefore the torque of the drive motor 150 can be directly transmitted to the stirring blade 134.

It is to be noted that unlike the drive device for the stirring device shown in FIG. 2, a drive shaft may be inserted from above the culture vessel and connected near the attaching portion of the stirring device to rotate the stirring device.

(Third Embodiment)

Figure 9:
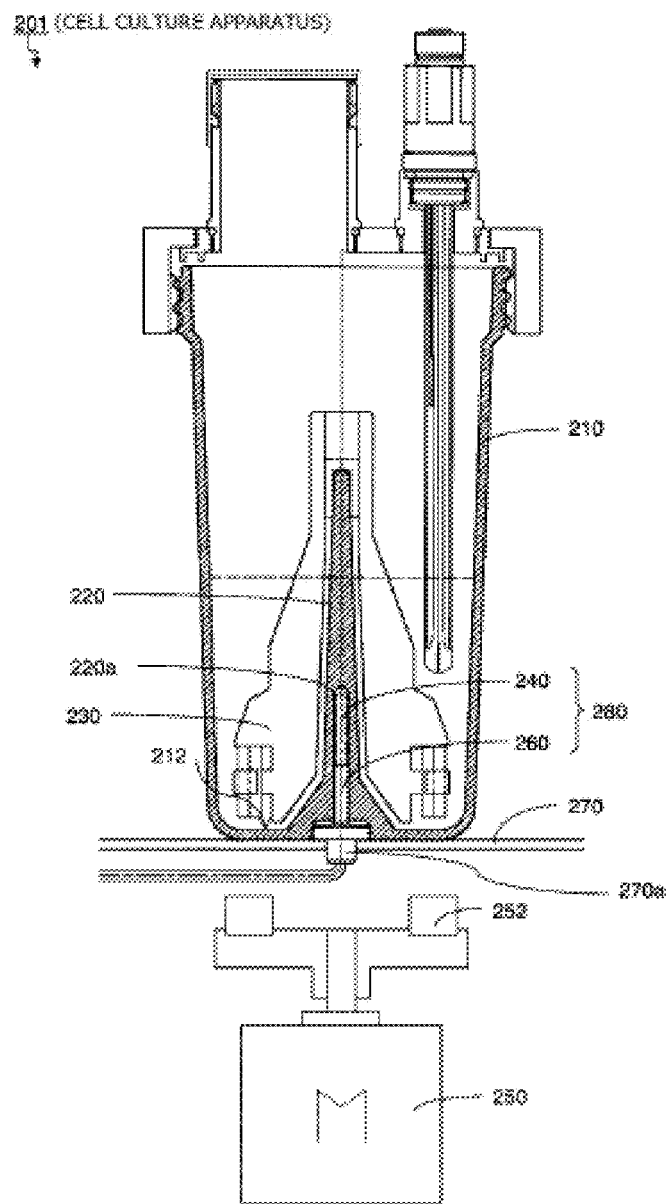
FIG. 9 is a sectional view illustrating the entire structure of a cell culture apparatus according to a third embodiment of the present invention.

FIG. 9 is a sectional view illustrating the entire structure of a cell culture apparatus 201 according to a third embodiment. The description of components similar to those of the cell culture apparatus 1 according to the first embodiment shown in FIG. 1 will not be repeated by giving similar reference numerals. The cell culture apparatus 201 includes a cylindrical culture vessel 210, a supporting column 220 fixed to stand upright in the culture vessel 210, and a stirring device 230 rotatably attached to the supporting column 220. The cell culture apparatus 201 is placed on a supporting stage 270 made of a magnetic permeable material. Under the supporting stage 270, a drive motor 250 and a drive device 252 as one example of a drive device are provided. In the third embodiment, the culture vessel 210 and the supporting column 220 are integrally formed.

The cell culture apparatus 201 according to the third embodiment shown in FIG. 9 is different from the cell culture apparatus 1 shown in FIG. 1 in that a hole 220a, into which a sheath tube (metal protective tube) 260 of a temperature sensor 280 is to be inserted, is drilled in the supporting column 220 from the outer surface side of a bottom 212 of the culture vessel 210. The sheath tube 260 is fixed to stand upright on the supporting stage 270 with, for example, an appropriate fixing member 270a.

It is to be noted that as the temperature sensor 280, one in which a temperature-sensitive part (temperature detector) 240 that senses temperature is incorporated in the tip of the tip-sealed sheath tube 260 is generally used.

The inner diameter of the hole 220a into which the sheath tube 260 is to be inserted and the thickness of the sheath tube 260, or the like, are not particularly limited are appropriately selected and determined. The inner diameter of the hole 220a is appropriately adjusted according to the outer diameter of the sheath tube 260 (incorporating the temperature-sensitive part 240 in its tip portion) to be inserted into the hole 220a. However, an appropriate clearance needs to be provided between the inner periphery of the hole 220a and the outer periphery of the sheath tube 260 to insert the sheath tube 260 without resistance, and the clearance is preferably about 0.1 mm. On the other hand, an excessive clearance may cause a measurement error. Further, providing such a clearance makes it possible to detachably attach the sheath tube 260 to the hole 220a.

Here, the hole 220a formed in the supporting column 220 has an inner diameter of, for example, 3.2 mm. The sheath tube 260 inserted into the hole 220a is formed from a stainless steel tube having an outer diameter of, for example, 3.0 mm. As described above, the temperature-sensitive part 240 of the temperature sensor 280 as one example of a device that measures the temperature of the culture liquid is inserted into the tip-sealed sheath tube 260 and placed at the tip of the tip-sealed sheath tube 260. Examples of the temperature-sensitive part 240 of the temperature sensor 280 include various resistance temperature detectors and thermocouples. The culture vessel 210 is placed in a predetermined position on the supporting stage 270, and the temperature-sensitive part 240 of the temperature sensor 280 is inserted into the hole 220a of the supporting column 220 from the outer surface side of the bottom of the culture vessel 210. More specifically, the sheath tube 260 incorporating the temperature-sensitive part 240 at its tip is inserted into the hole 220a of the supporting column 220. At this time, the temperature-sensitive part 240 of the temperature sensor 280 is placed, for example, about 20 to 30 mm away from the inner surface of the bottom 212 of the culture vessel 210. However, the clearance between the temperature-sensitive part 240 and the inner surface of the bottom 212 is not limited to 20 to 30 mm, and is appropriately selected according to the outer diameter or shape of the supporting column 220, the thickness of the sheath tube 260, etc. In the cell culture apparatus 201 according to the third embodiment having such a structure, the temperature-sensitive part 240 of the temperature sensor 280 is placed in a position where the temperature of the culture liquid can be properly measured without any external influence, and therefore the temperature of the culture liquid can be monitored during culture. It is to be noted that the temperature-sensitive part 240 of the temperature sensor 280 may be directly attached from the outer surface side of the bottom 212 of the culture vessel 210 without passing through the supporting stage 270 (not shown).

When the temperature of the culture liquid is measured, an electric signal from the temperature-sensitive part 240 incorporated in the sheath tube 260 of the temperature sensor 280 is sent to a temperature measuring instrument (not shown) through a lead wire and then displayed and recorded as a temperature reading.

It is to be noted that the temperature sensor 280 is well known, and for example, a commercially-available one is effectively used.

(Fourth Embodiment)

Figure 10:
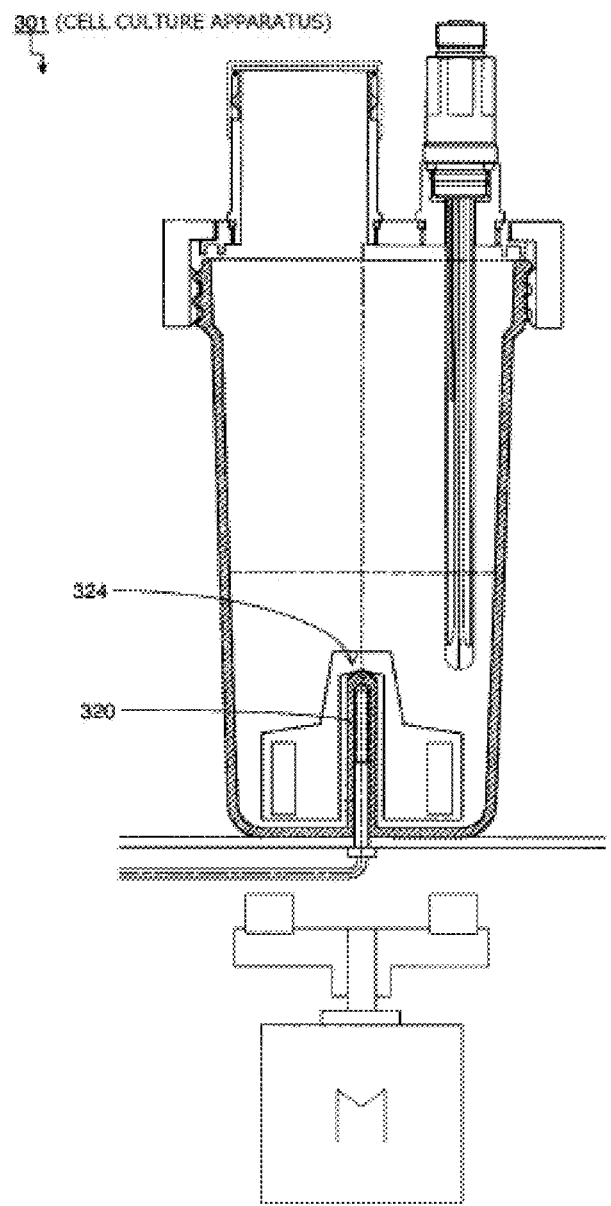
FIG. 10 is a sectional view illustrating the entire structure of a cell culture apparatus according to a fourth embodiment of the present invention.

FIG. 10 is a sectional view illustrating the entire structure of a cell culture apparatus 301 according to a fourth embodiment. In the cell culture apparatus 201 according to the third embodiment shown in FIG. 9, the supporting column 220 has a shape such that its lower part is thick and its diameter gradually decreases from its bottom to top, but the cell culture apparatus 301 according to the fourth embodiment shown in FIG. 10 is different from the cell culture apparatus 201 in that a supporting column 320 has the same outer diameter in its axial direction. The cell culture apparatus 301 is different from the cell culture apparatus 201 also in that an upper portion 324 of the supporting column 320 is located below the liquid level of the culture liquid. The cell culture apparatus 301 having such a structure also can monitor the temperature of the culture liquid during culture.

Cells to be cultured in the cell culture apparatus according to the present invention are not particularly limited, and examples thereof include cells of animals, insects, and plants and filamentous microorganisms such as filamentous fungi and actinomycete. Among them, animal cells are advantageous in that many kinds of animal cells are commercially available. Examples of a source of animal cells include, but are not limited to, humans, monkeys, dogs, cats, rabbits, rats, nude mice, mice, guinea pigs, pigs, sheep, Chinese hamsters, cows, marmosets, and African green monkeys.

The type of cells to be cultured using the cell culture apparatus according to the present invention is not particularly limited, but the cell culture apparatus according to the present invention is preferably used to culture cells whose growth is influenced by shear stress, because the effects of the present invention are exhibited. Examples of such cells include pluripotent stem cells (e.g., ES cells, iPS cells) and stem cells such as neural stem cells. These cells form cell aggregates, and therefore can grow while maintaining their undifferentiated state. Any cells can be appropriately used without particular limitation as long as they are highly sensitive to shear stress. Further, differentiation of stem cells into cells of another tissue can be induced while the stem cells are allowed to grow while maintaining their undifferentiated state.

It is to be noted that the cell culture apparatus according to the present invention can be made disposable.

A cell culture method using the cell culture apparatus according to the present invention includes a first process in which cells that form cell aggregates are inoculated into the culture vessel together with a culture medium and a second process in which the cells are cultured by rotating the stirring device at a speed such that cell aggregates do not precipitate on the bottom of the culture vessel and are not broken up. This cell culture method makes it possible to easily and reproducibly obtain a population of cell aggregates uniform in particle size.

This cell culture method using the cell culture apparatus according to the present invention will be described later in detail with reference to Experimental Examples. The first process will be described in, for example, the sections "Cells, culture medium, and reagents used" and "Culture method using cell culture apparatus" in Experimental Example 1, the second process will be described in, for example, the section "Amplification culture of iPS cells in cell culture apparatus" in Experimental Example 1, and the results of culture will be described in the section "Results" in Experimental Example 1. These descriptions will be made also in Experimental Example 2.

The cell culture method using the cell culture apparatus according to the present invention may further include, when the cells that form cell aggregates are pluripotent stem cells, a third process, in which the cells are cultured by adding, to the culture medium, a factor that induces differentiation into somatic cells, in addition to the first and second processes to induce differentiation of the pluripotent stem cells into somatic cells. This cell culture method makes it possible to easily and reproducibly obtain a population of cell aggregates uniform in particle size and to efficiently induce differentiation of pluripotent stem cells into somatic cells.

The cell culture method that induces differentiation of pluripotent stem cells into somatic cells with the use of the cell culture apparatus according to the present invention will be described later in detail with reference to Experimental Examples. The first process and the second process will be described in, for example, the sections "Cells, culture media, and reagents used" and "Process of formation of embryoid bodies from iPS cells" in Experimental Example 3, the third process will be described in, for example, the section "Process of induction of differentiation of iPS cells into cardiomyocytes" in Experimental Example 3, and the results of culture will be described in the section "Results" in Experimental Example 3. These descriptions will be made also in Experimental Example 4.

EXAMPLES

Hereinbelow, a method for culturing/amplifying cells by utilizing the present invention will be described in more detail based on the following Experimental Examples, but these Experimental Examples are not intended to limit the present invention.

Experimental Example 1

Human iPS cells were cultured and amplified using the cell culture apparatus according to the present invention. An example of the experiment will be described below.
(Cells, Culture Medium, and Reagents Used)
Cells: Mouse embryo fibroblasts (ReproCELL Incorporated) and Human iPS cells 201B7 and 253G1
(RIKEN)
Culture medium: Medium for primate ES/iPS cells (trade name: Primate ES Cell Medium, ReproCELL Incorporated)
Reagents: Recombinant human fibroblast basic growth factor (general name: bFGF, ReproCELL Incorporated), Cell detachment solution for ES/iPS cells (trade name: CTK solution, ReproCELL Incorporated), Phosphate buffered saline (Life Technologies), Cell dissociation solution (trade name: AccuMax, Merk Millipore), Serum-free maintenance medium for human ES/iPS cells (trade name: mTeSR1, STEMCELL TECHNOLOGIES), and Y-27632 (general name for compound, Calbiochem)
(Culture Method Using Cell Culture Apparatus)

Examples of a method for preparing iPS cells to be cultured in the cell culture apparatus according to the present invention include: (1) inoculation of cell aggregates and (2) inoculation of single cell suspension, and the methods (1) and (2) will be described later. However, a method used when cells to be cultured in the cell culture apparatus according to the present invention are prepared is not limited to the method (1) or (2), and a well-known method may be appropriately used according to the type or state of cells to be amplified.

(1) Inoculation of Cell Aggregates

Human iPS cells cultured on mouse embryo fibroblasts (in ten 10-cm culture dishes) were prepared. The human iPS cells were cultured in a medium for primate ES/iPS cells (Primate ES Cell Medium) containing recombinant human fibroblast basic growth factor (10 ng/ml) in 10-cm cell culture dishes. The culture medium was removed by aspiration, and then 10 mL of phosphate buffered saline was added to each of the culture dishes and quickly removed by aspiration. Then, 0.5 mL of a cell detachment solution for ES/iPS cells (CTK solution) was added to each of the culture dishes, and the culture dishes were allowed to stand in a $CO_2$ incubator at 37° C. for 10 minutes. The dissociation solution for ES/iPS cells (CTK solution) was removed by aspiration, and 4 mL of a medium for primate ES/iPS cells (Primate ES Cell Medium) containing recombinant human fibroblast basic growth factor (10 ng/mL) was added to each of the culture dishes. Then, cell aggregates were collected from the culture dishes by pipetting and transferred into a 50-mL conical tube. Then, the conical tube was centrifuged at 190 G at room temperature for 3 minutes, and the supernatant was removed by aspiration and the residue was again suspended in 100 mL of a serum-free maintenance medium for human ES/iPS cells (mTeSR1). Then, 10 μM of Y27632 was added, and 100 mL of the culture liquid was inoculated into the vessel (culture vessel) according to the present invention having a full capacity of 250 mL. It is to be noted that culture conditions shall be the same as those used in a well-known method and are not particularly limited.

(2) Inoculation of Single Cell Suspension

The cell aggregates prepared by the method (1) were centrifuged at 190 G at room temperature for 3 minutes, and the supernatant was removed by aspiration and the residue was again suspended in phosphate buffered saline added (the amount of the phosphate buffered saline added was 4 mL per 10-cm culture dish). The suspension was again centrifuged at 190 G at room temperature for 3 minutes, and the phosphate buffered saline was removed by aspiration. Then, a cell dissociation solution (AcuuMax) was added (the amount of the cell dissociation solution added was 1 mL per 10-cm culture dish) to the residue, and the mixture was subjected to shaking culture in an incubator at 37° C. for 10 minutes. Then, the cell aggregates were sufficiently dissociated into single cells by pipetting, and then mTeSR1 was added in the same amount as the cell dissociation solution (AcuuMax). The mixture was centrifuged at 190 G at room temperature for 3 minutes, and the supernatant was removed by aspiration and the residue was again suspended in 10 mL of a serum-free maintenance medium for human ES/iPS cells (mTeSR1) to count the number of cells. Then, $2 \times 10^7$ cells were taken and diluted with a serum-free maintenance medium for cells (mTeSR1) to 100 mL in a measuring cylinder to obtain a cell suspension. Then, 10 µM of Y27632was added to the cell suspension, and the cell suspension was inoculated into the 250-mL vessel.

(Amplification Culture of iPS Cells in Cell Culture Apparatus)

Figure 3:
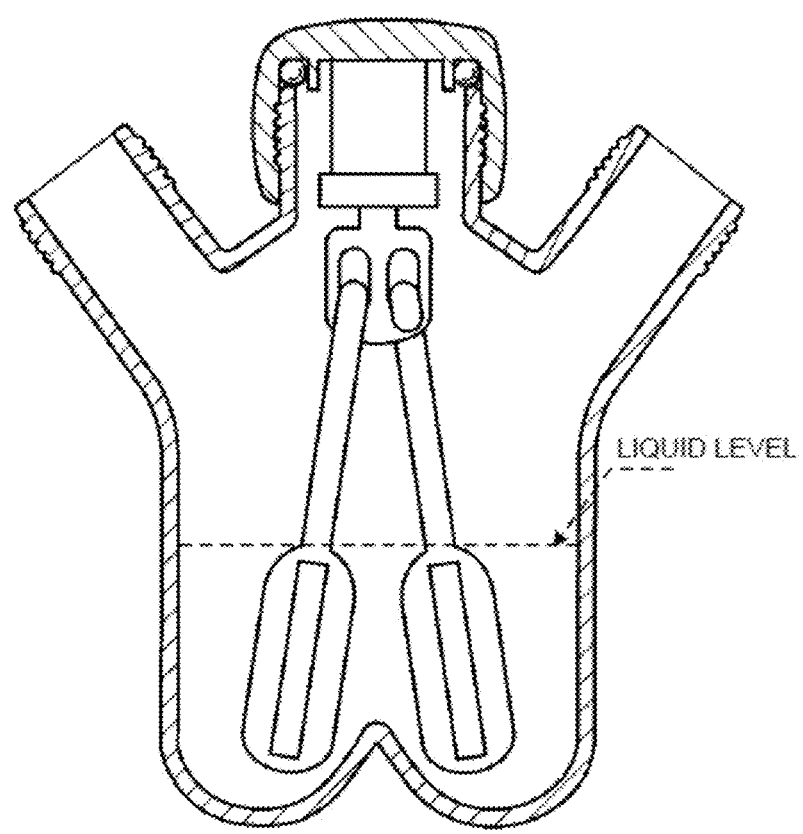
FIG. 3 is a schematic sectional view of a cell culture apparatus manufactured by INTEGRA as one example of a cell culture apparatus in which a horizontal flow is created by rotating a stirring shaft having a thick bulb-shaped tip.

For a comparison purpose, iPS cells prepared by the above method were cultured in both the cell culture apparatus according to the present invention and a cell culture apparatus manufactured by INTEGRA (cell culture apparatus described above in the section of Background Art with reference to laminar-flow culture, in which "a horizontal flow is created by rotating a stirring shaft having a thick bulb-shaped tip) (see FIG. 3) as a comparative example.

It is to be noted that the full capacity of the vessel of the cell culture apparatus manufactured by INTEGRA is the same as that of the cell culture apparatus according to the present invention. The inoculated amount was also the same. In both cases, culture was performed in an incubator with 5% $CO_2$ at 37° C. and 40 rpm. The culture medium was completely replaced every 24 hours. Y27632 was not added on and after the day following the day on which culture was started.

(Results)

Figure 5:
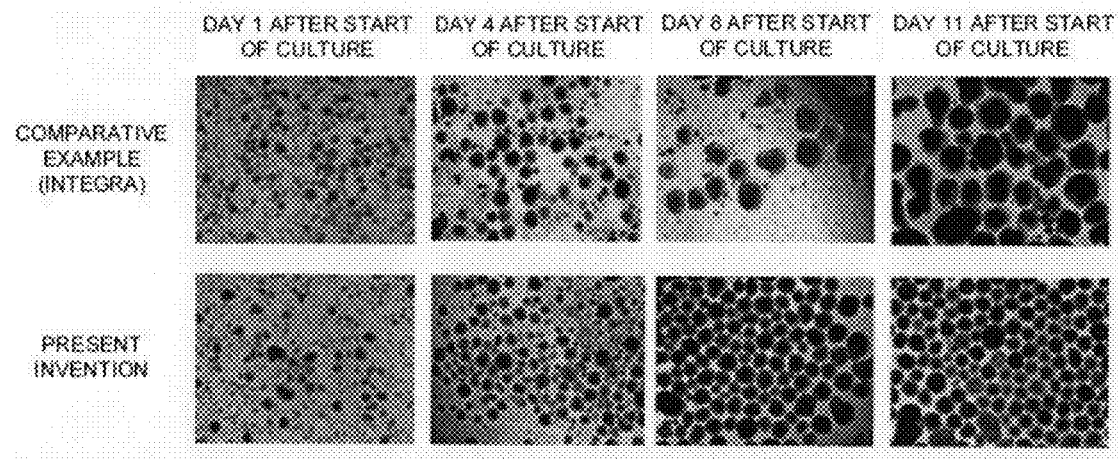
FIG. 5 illustrates temporal changes in the shape of embryoid bodies from human iPS cells which were determined in Experimental Example 1 by using different stirring impellers, wherein photographs of Comparative Example and photographs of the present invention are at the same magnification.

The cell culture apparatus according to the present invention and the cell culture apparatus manufactured by INTEGRA were used to culture human iPS cells to determine their applicability to suspension culture of human iPS cells. The results of culture are shown in FIG. 5. FIG. 5 illustrates temporal changes in the shape of embryoid bodies from human iPS cells, which were determined by using different stirring impellers. Human iPS cells were inoculated in the form of cell aggregates, and the shape of embryoid bodies was evaluated with time. When human iPS cells were inoculated in the form of cell aggregates into the cell culture apparatus according to the present invention, many uniform embryoid bodies (100 to 300 µm) were observed on and after day 3 after the start of culture. On the other hand, when human iPS cells were inoculated in the form of cell aggregates into the cell culture apparatus manufactured by INTEGRA, embryoid bodies were formed, but as can be seen from FIG. 5, the embryoid bodies had a large diameter (500 µm or more) and the number of embryoid bodies was significantly small. In both cases, the stirring impeller was rotated at 40 rpm, which allows culture at a low shear stress in a laminar flow but usually causes stagnation in the center of the culture vessel due to low-speed stirring. In the case of the cell culture apparatus manufactured by INTEGRA, an increase in the amount of cell aggregates that accumulate (precipitate) in the center of its culture vessel with time is observed, which is considered to be a cause of the reduction in the number of embryoid bodies and the increase in the diameter of embryoid bodies. On the other hand, the cell culture apparatus according to the present invention allows culture at a low shear stress and has a system added to prevent the accumulation of cell aggregates in the center of its culture vessel, which is considered to have contributed to effective formation of embryoid bodies and amplification of cells.

It is to be noted that there was no difference in the results of amplification culture using the cell culture apparatus according to the present invention between when iPS cells prepared by the method (1) utilizing inoculation of cell aggregates were used and when iPS cells prepared by the method (2) utilizing inoculation of single cell suspension were used. For this reason, in Experimental Example 2, iPS cells prepared by the method (2) utilizing inoculation of single cell suspension were used.

Experimental Example 2

Figure 4:
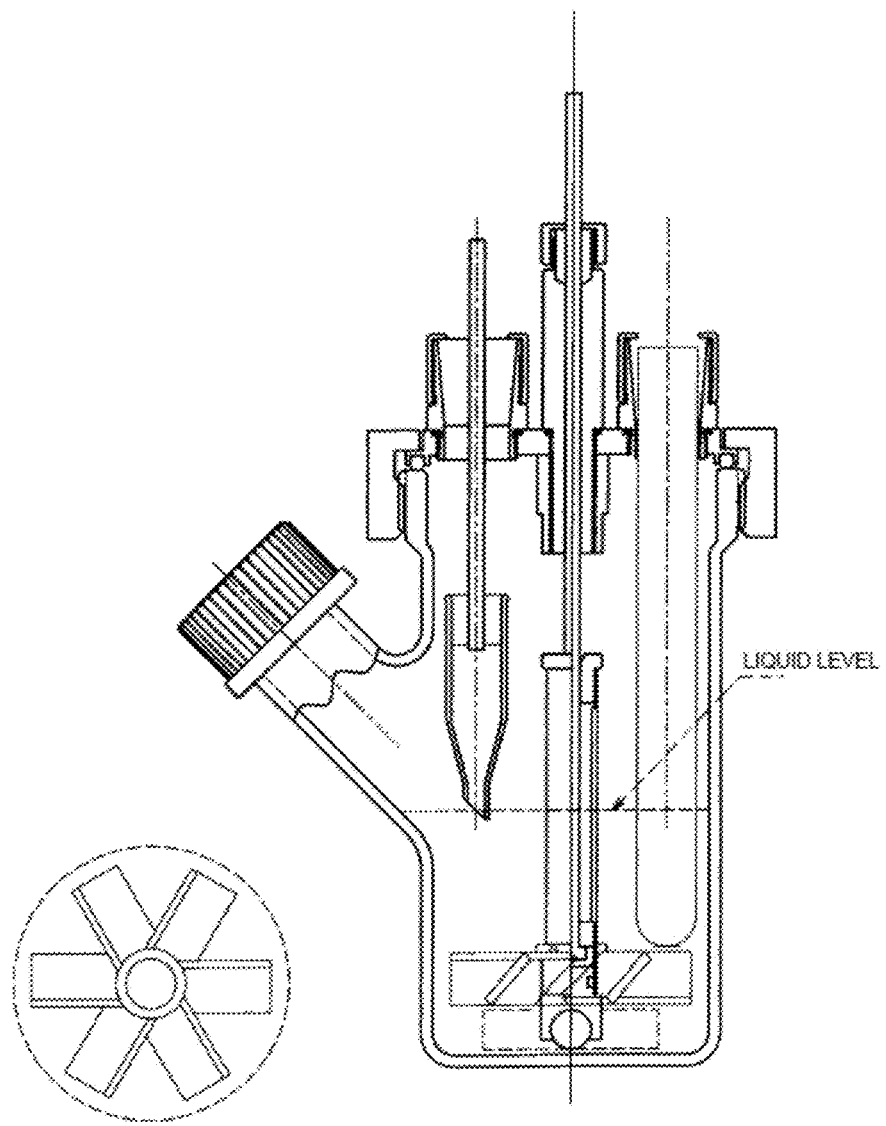
FIG. 4 is a schematic sectional view of a cell culture apparatus equipped with a paddle-type stirring impeller as one example of a cell culture apparatus equipped with a stirring impeller having two or more blades attached at a given inclination angle with respect to a stirring shaft.

A comparison was made also between the cell culture apparatus according to the present invention and a cell culture apparatus equipped with a usually-used 6 paddle-type stirring impeller (upward flow, downward flow) (cell culture apparatus described above in the section of Background Art with reference to axial-flow culture, which is equipped with "a stirring impeller having two or more blades attached at a given inclination angle with respect to a stirring shaft") (see FIG. 4) in the same manner as in Experimental Example 1. In this experiment, culture was performed at 40 rpm, 37° C., pH 7.2, and 40% oxygen saturation.

Figure 6A:
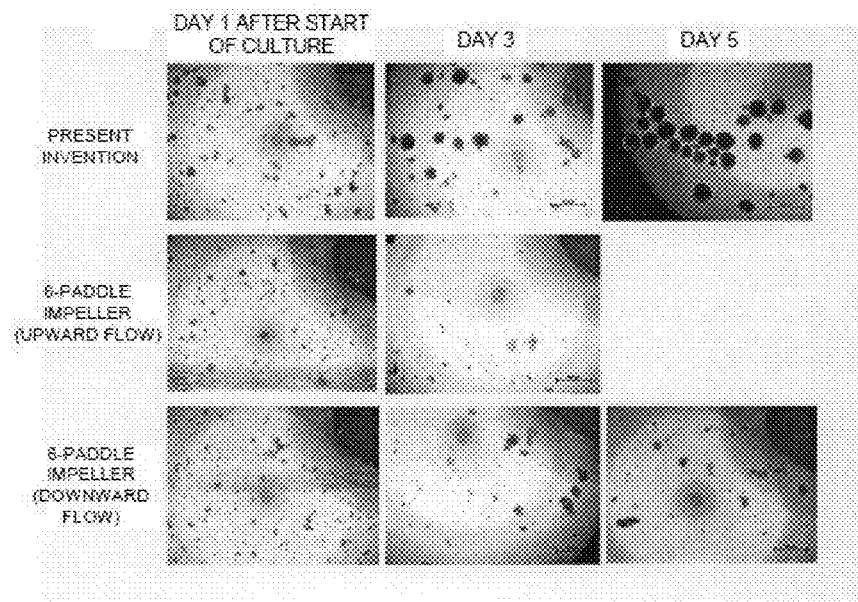
FIG. 6A illustrates temporal changes in the shape of embryoid bodies from human iPS cells which were determined in Experimental Example 2 by using different stirring impellers.
Figure 6B:
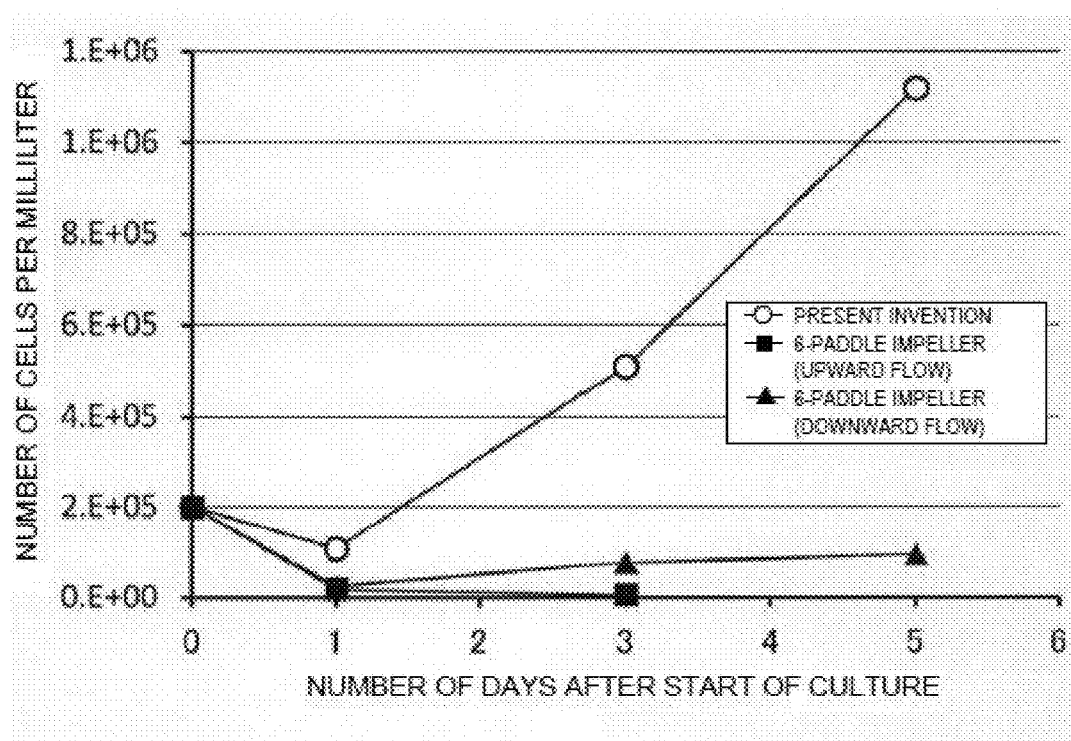
FIG. 6B illustrates temporal changes in the number of human iPS cells which were determined in Experimental Example 2 by using different stirring impellers.

The comparison results are shown in FIG. 6. FIG. 6A illustrates temporal changes in the shape of embryoid bodies from human iPS cells, which were determined using different stirring impellers. FIG. 6B illustrates temporal changes in the number of human iPS cells, which were determined using different stirring impellers. When human iPS cells were inoculated in the form of a single cell suspension into the cell culture apparatus according to the present invention, embryoid bodies uniform in particle size were formed as when human iPS cells were inoculated in the form of cell aggregates, and the number of cells was increased with time and reached $2\times10^6$ cells/mL on day 5 after the start of culture ($2\times10^8$: ten times the number of inoculated cells). On the other hand, when human iPS cells were inoculated in the form of a single cell suspension into the cell culture apparatus equipped with a paddle-type stirring impeller facing upward or downward, embryoid body formation was not promoted and cell growth was not observed, either. As described above, a laminar flow is created by stirring at 40 rpm in the cell culture apparatus according to the present invention, but an axial flow is observed in the cell culture apparatus equipped with a 6 paddle-type stirring impeller. It is considered that, unlike a laminar flow, shear stress in vertical and horizontal directions caused by an axial flow is unsuitable for the growth of human iPS cells.

In Experimental Examples 1 and 2, as a result of cell culture using the cell culture apparatus according to the present invention, marker genes for undifferentiated iPS cells, such as OCT3/4, NANOG, SOX2, TRA-1-60, and SSEA-4, were expressed in almost all the cells within the embryoid bodies observed on day 5 after the start of culture in both cases where iPS cells were prepared by the method utilizing inoculation of cell aggregates and where iPS cells were prepared by the method utilizing inoculation of single cells. Further, when the cells were analyzed by flow cytometry, about 99% of the cells were positive for SSEA-4, but on the other hand, SSEA-1 as a differentiation marker was not observed. From this, it was considered that human iPS cells were amplified in the cell culture apparatus according to the present invention while maintaining their undifferentiated state.

Experimental Example 3

Differentiation of iPS cells into cardiomyocytes was induced by utilizing the cell culture apparatus according to the present invention.

(Cells, Culture Media, and Reagents Used)

Cells: Mouse embryo fibroblasts (ReproCELL Incorporated) and Human iPS cells 253G1 (RIKEN)

Culture medium: Medium for primate ES/iPS cells (trade name: Primate ES Cell Medium, ReproCELL Incorporated)

Reagents: Recombinant human fibroblast basic growth factor (general name: bFGF, ReproCELL Incorporated), Dissociation solution for ES/iPS cells (trade name: CTK solution, ReproCELL Incorporated), Phosphate buffered saline (Life Technologies), Serum-free maintenance medium for human ES/iPS cells (trade name: mTeSR1, STEMCELL TECHNOLOGIES), Y-27632 (general name for compound, Calbiochem), Recombinant human activin-A (R&D Systems), Recombinant human bone morphogenetic protein 4 (general name: BMP-4, R&D Systems), Recombinant human vascular endothelial cell growth factor (general name: VEGF, R&D Systems), and Wnt signaling pathway inhibitor IWR-1 (Sigma-Aldrich)

Basal medium for cardiomyocyte differentiation: one containing the following 1) to 4):

1) Serum-free medium for human hematopoietic stem cells (trade name: StemPro-34, Life Technologies);
2) 1-Thioglycerol (final concentration: 400 μM, Sigma-Aldrich);
3) Ascorbic acid (final concentration: 50 μg/mL, Wako Pure Chemical Industries, Ltd.); and
4) L-glutamine (final concentration: 2 mM, Life Technologies)

(Process of Formation of Embryoid Bodies from iPS Cells)

Figure 7:
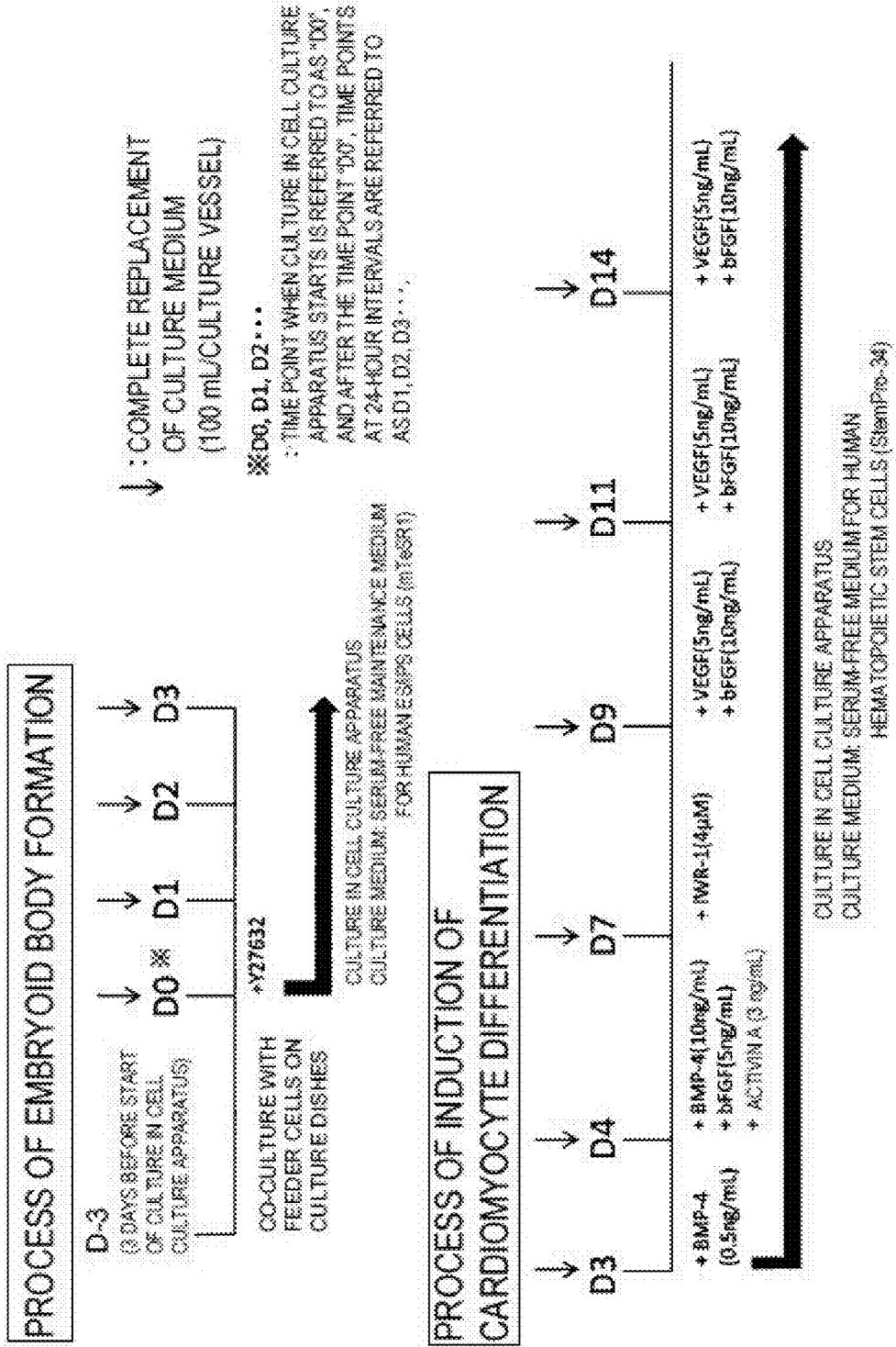
FIG. 7 illustrates a culture procedure for inducing differentiation of iPS cells into cardiomyocytes in Experimental Example 3.

(1) Cell aggregates prepared by inoculation of cell aggregates in the same manner as in Experimental Example 1 were inoculated into the cell culture apparatus according to the present invention and cultured. The results are shown in FIG. 7. FIG. 7 illustrates a culture procedure for inducing differentiation of iPS cells into cardiomyocytes. It is to be noted that in FIG. 7, "D0" represents a time point when cells are inoculated into the cell culture apparatus according to the present invention, and after the time point "D0", time points at 24-hour intervals are referred to as "D1", "D2", . . . .

(Process of Inducing Differentiation of iPS Cells into Cardiomyocytes)

Induction of differentiation of iPS cells into cardiomyocytes was performed by reference to a method described by Willems et al. in Circulation Research, USA, American Heart Association, Jul. 7, 2011, 109 (4), p. 360-364 (see Non-Patent Literature 4). Culture was performed using the cell culture apparatus according to the present invention based on a schedule shown in FIG. 7. A specific procedure for the culture will be described below.

Culture was performed for 3 days in the cell culture apparatus according to the present invention (FIG. 7, D3). Then, the culture medium was completely replaced with 100 mL of a basal medium for cardiomyocyte differentiation containing recombinant human bone morphogenetic protein 4 (BMP-4, 0.5 ng/mL), and culture was performed in the cell culture apparatus according to the present invention (rotation speed: 40 rpm, pH: 7.2, temperature: 37° C., dissolved oxygen: 40% oxygen saturation; hereinafter, culture was performed with stirring under the same conditions). After one day, (FIG. 7, D4), the culture medium was completely replaced with 100 mL of a basal medium for differentiation containing recombinant human bone morphogenetic protein 4 (BMP-4, 10 ng/mL), recombinant human fibroblast basic growth factor (bFGF, 5 ng/mL), and activin-A (3 ng/mL), and culture was performed in the cell culture apparatus according to the present invention. After 3 days (FIG. 7, D7), the culture medium was completely replaced with 100 mL of a basal medium for differentiation containing Wnt signaling pathway inhibitor IWR-1 (4 μM), and culture was performed in the cell culture apparatus according to the present invention. After 2 days (D9), the culture medium was completely replaced with 100 mL of a basal medium for differentiation containing recombinant human vascular endothelial cell growth factor (VEGF, 5 ng/mL) and recombinant human fibroblast basic growth factor (bFGF, 10 ng/mL), and culture was performed in the cell culture apparatus according to the present invention. After 2 days (D11), the culture medium was completely replaced with 100 mL of a basal medium for differentiation containing recombinant human vascular endothelial cell growth factor (VEGF, 5 ng/mL) and recombinant human fibroblast basic growth factor (bFGF, 10 ng/mL), and culture was performed in the cell culture apparatus according to the present invention. After 3 days (D14), the culture medium was completely replaced with 100 mL of a basal medium for differentiation containing vascular endothelial cell growth factor (VEGF, 5 ng/mL) and recombinant human fibroblast basic growth factor (bFGF, 10 ng/mL), and culture was performed in the cell culture apparatus according to the present invention.

(Results)

As described above, after the 3-day process of embryoid body formation using a serum-free maintenance medium for cells (trade name: mTeSR1), cardiomyocyte differentiation was induced using various growth factors and low-molecular compounds. As a result, embryoid body formation was maintained by performing culture in the cell culture apparatus according to the present invention irrespective of the fact that medium conditions were changed. On the other hand, in the cell culture apparatus, manufactured by INTEGRA, as a comparative example, aggregation of embryoid bodies and accumulation of cell aggregates in the center of the culture vessel were observed as in the case of the above-described culture of undifferentiated iPS cells, and therefore cell culture could not be maintained.

Figure 8:
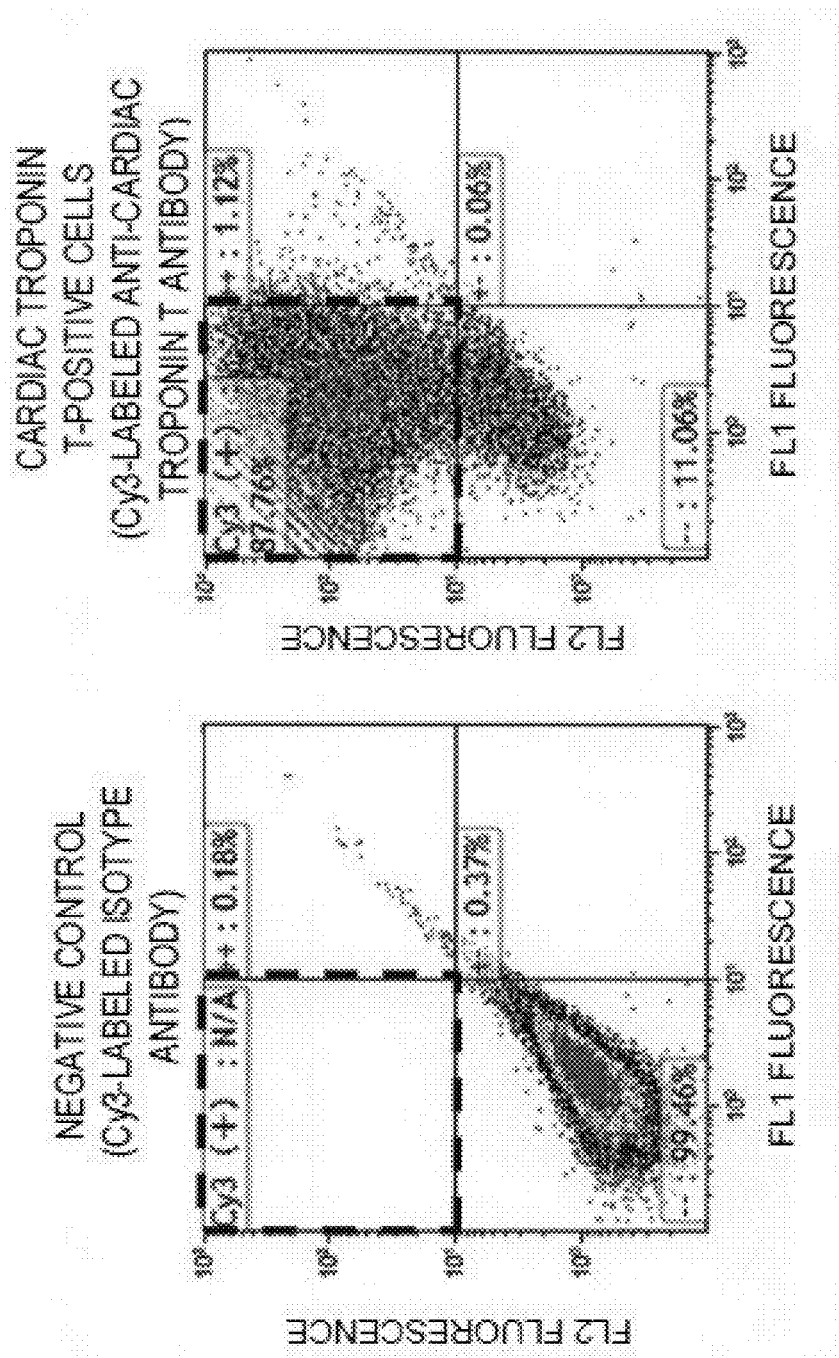
FIG. 8 illustrates histograms of flow cytometry showing the ratio of cardiomyocytes differentiated from iPS cells in Experimental Example 3.

In the case of cell culture using the cell culture apparatus according to the present invention, spontaneous beating was observed in almost all the embryoid bodies on day 11 (FIG. 7, D14) after the start of induction of cardiomyocyte differentiation. The cells were analyzed by flow cytometry using an antibody against cardiac troponin T as a cardiomyocyte marker and an antibody against CD31 as a vascular endothelial cell marker. The results are shown in FIG. 8. FIG. 8 illustrates histograms of flow cytometry showing the ratio of cardiomyocytes differentiated from iPS cells. In FIG. 8, the histogram on the left shows the result of a negative control, and the histogram on the right shows the detection of cardiac troponin T-positive cells. The cardiac troponin T-positive cells were detected using a Cy3-labeled anti-cardiac troponin T antibody. Since the autofluorescence of cells was detected (FL1 fluorescence), cells negative for FL1 but positive for FL2 in the histogram on the right were regarded as cardiac troponin T-positive cells. More specifically, cells present in a region enclosed with a dotted line in the histogram on the right are cells expressing cardiac troponin T. As shown in FIG. 8, 80 to 90% of the cells were cardiomyocytes positive for cardiac troponin T, and 5 to 6% of the cells were vascular endothelial cells positive for CD31. When the cells were inoculated on a temperature-responsive culture dish (manufactured by CellSeed Inc. under the trade name of UpCell (registered trademark)), spontaneous beating of cardiomyocytes was observed on the following day, and spontaneous and synchronous contraction of all the cardiomyocytes on the culture dish was observed on day 5 after the inoculation, and a cell sheet was formed by temperature drop treatment. Further, as in the result of flow cytometry, 80 to 90% of the cells in the cell sheet were positive for cardiac troponin T and sarcomeric actinin and had a clear striated structure. From this, it was confirmed that differentiation into mature cardiomyocytes and formation of functional tissue were achieved.

Experimental Example 4

Differentiation of mouse ES cells into cardiomyocytes was induced by utilizing the cell culture apparatus according to the present invention. The differentiation induction was performed in the same manner as in Experimental Example 3 except that mouse ES cells were used. As a result, as in the case of Experimental Example 3, embryoid bodies uniform in size were obtained, and as a result, 80 to 90% of the cells were differentiated into cardiomyocytes positive for cardiac troponin T. From this, it was confirmed that there is no difference in the effect of the present invention between iPS cells and ES cells.

REFERENCE SIGNS LIST 1, 101, 201, 301: cell culture apparatus
10, 110, 210: culture vessel
12, 112, 212: bottom
14, 114: inner side surface
20, 120, 220, 320: supporting column
22, 122: conical portion
22a: O-ring
22b: screw
24, 124, 324: upper portion
30, 130 230: stirring device
32, 132: attaching portion
34, 134: stirring blade
36: magnetic body
40: pH sensor (measuring device)
50, 150, 250: drive motor (drive device)
52, 252: another magnetic body (drive device)
154: drive shaft (drive device)
220a: hole
240: temperature-sensitive part
260: sheath tube
270: supporting stage
270a: fixing member
280: temperature sensor

What is claimed:

1. A cell culture apparatus comprising:
a cylindrical culture vessel that holds a culture liquid containing cells;
a supporting column that is fixed to stand upright in a center of an inner surface of a bottom of the culture vessel; and
a stirring device comprising an attaching portion that is attached to an upper portion of the supporting column so as to be rotatable relative to the supporting column and a stirring blade, an upper portion of the stirring blade being fixed to the attaching portion so as to rotate around the supporting column as a center of rotation, the stirring blade of the stirring device having a plate shape extending downwards, as a whole, from the upper portion of the stirring blade, wherein
the supporting column has a conical portion, the conical portion having a portion conically formed to rise up from the inner surface of the bottom and the conical portion having a diameter increasing toward the inner surface of the bottom,
the upper portion of the supporting column is located above a liquid level of the culture liquid, and
the stirring blade of the stirring device is formed so that a lower portion of the stirring blade has a shape that conforms to an outer surface of the conical portion of the supporting column when the stirring device rotates.

2. The cell culture apparatus according to claim 1, wherein
the stirring blade of the stirring device is formed to have a shape that conforms to the inner surface of the bottom in the culture vessel when the stirring device rotates.

3. The cell culture apparatus according to claim 1, wherein
the stirring blade of the stirring device is formed to have a shape that conforms to an inner side surface of the culture vessel when the stirring device rotates.

4. The cell culture apparatus according to claim 1, further comprising a drive device that rotates the stirring blade of the stirring device without direct contact with the culture liquid.

5. The cell culture apparatus according to claim 4, wherein
the stirring blade of the stirring device has a magnetic body fixed to its lower end,
the drive device provided below the culture vessel comprises a drive device that is another magnetic body that is horizontally rotated in a position opposed to the magnetic body with the bottom of the culture vessel interposed therebetween, and
the stirring blade is horizontally rotated by rotating the another magnetic body.

6. The cell culture apparatus according to claim 4, wherein
the drive device is provided below the culture vessel, and
a drive shaft of the drive device passes through an inside of the supporting column, extends to the upper portion of the supporting column, and is attached to the stirring blade of the stirring device at the upper portion.

7. The cell culture apparatus according to claim 1, wherein
the supporting column has, in its inside, a hole into which a temperature-sensitive part of a temperature sensor that measures a temperature of the culture liquid is inserted from an outer surface side of the bottom of the culture vessel.

8. The cell culture apparatus according to claim 7, further comprising the temperature-sensitive part of the temperature sensor.

9. The cell culture apparatus according to claim 7, wherein
the temperature-sensitive part of the temperature sensor is placed 20 to 30 mm away from an outer surface of the bottom of the culture vessel.

10. The cell culture apparatus according to claim 8, wherein
the temperature-sensitive part of the temperature sensor is placed 20 to 30 mm away from an outer surface of the bottom of the culture vessel.

11. A cell culture method using the cell culture apparatus according to claim 1, comprising:
a first process in which cells that form cell aggregates are inoculated into the culture vessel together with a culture medium; and
a second process in which the cells are cultured by rotating the stirring device at a speed such that cell aggregates do not precipitate on the inner surface of the bottom of the culture vessel and that the cell aggregates are not broken up, wherein
the cells are cultured while the cell aggregates maintain their uniform particle size.

12. The cell culture method according to claim 11, further comprising, when the cells that form cell aggregates are pluripotent stem cells, a third process in which the cells are cultured by adding, to the culture medium, a factor that induces differentiation into somatic cells, wherein differentiation of the pluripotent stem cells into somatic cells is induced.

\* \* \* \* \*